US00PP12517P2

(12) United States Plant Patent
Noodelijk

(10) Patent No.: US PP12,517 P2
(45) Date of Patent: Apr. 2, 2002

(54) CHRYSANTHEMUM PLANT NAMED 'CACHI DARK'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/561,961

(22) Filed: May 1, 2000

(51) Int. Cl.[7] ..... A01H 5/00
(52) U.S. Cl. ..... Plt./295
(58) Field of Search ..... Plt./295

(56) References Cited

PUBLICATIONS

UPOV–ROM GTITM Computer Database 2001/01, GTI JOUVE Retrieval Software, citation(s) for 'Cachi Dark' Feb. 6, 2001.*

* cited by examiner

*Primary Examiner*—Bruce R. Campell
*Assistant Examiner*—Annette H. Para
(74) *Attorney, Agent, or Firm*—Parkhurst & Wendel, L.L.P.

(57) ABSTRACT

A Chrysanthemum plant named 'CACHI DARK' characterized by its small sized blooms with yellow ray-florets and yellow disc florets with brown tips.

2 Drawing Sheets

RELATED CULTIVARS

'CACHI DARK' is related to CACHI (U.S. Plant patent application Ser. No. 09/276,699). 'CACHI DARK' is a color mutant of Cachi.

BACKGROUND OF THE INVENTION

'CACHI DARK' is a product of a breeding and selection program which had the objective of finding color mutants of CACHI. The new plant of the present invention comprises a new and distinct cultivar of chrysanthemum plant that is a natural occuring sport of a parent chrysanthemum named CACHI. A comparison with Parent chrysanthemum CACHI is also made in this application. The new cultivar was discovered as a whole plant mutation in April 1998 by Rob Noodelijk in a controlled environment (greenhouse) in Rijsenhout Holland. The first act of asexual reproduction of 'CACHI DARK' was accomplished when vegetative cuttings were taken from the initial selection in June 1998 in Rijsenhout Holland.

SUMMARY OF THE INVENTION

The present invention is a new and distinct variety of chry santhemum bearing small sized blooms with yellow ray-florets and disc florets grown to a cushion of yellow color with brown tips.

BRIEF DESCRIPTION OF THE DRAWINGS

The present invention of a new and distinct variety of chry santhemum is shown in the accompanying drawings, the color being as nearly true as possible with color photographs of this type.

DESCRIPTION OF THE INVENTION

Figure 1:
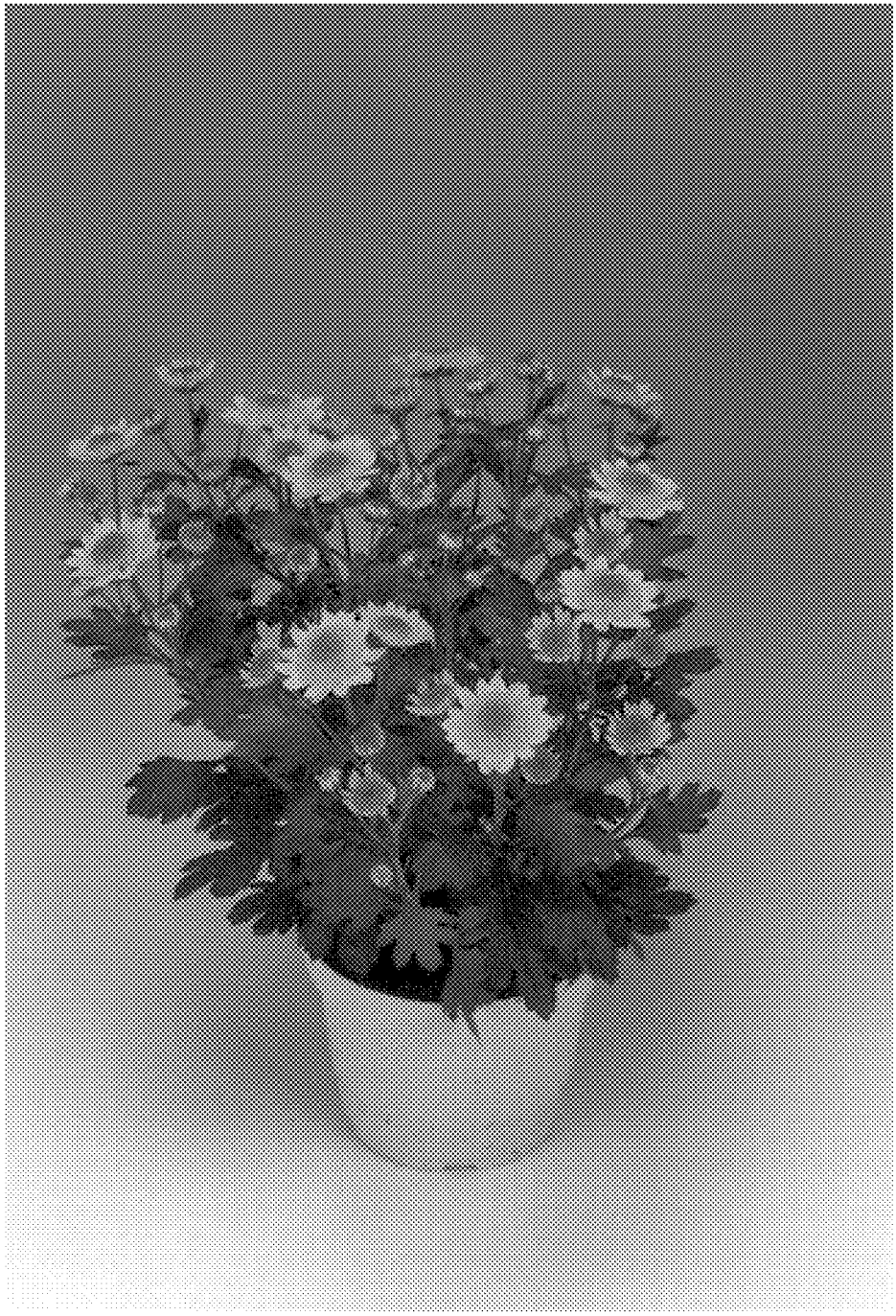
FIG. 1 shows a plant of the cultivar in full bloom.
Figure 2:
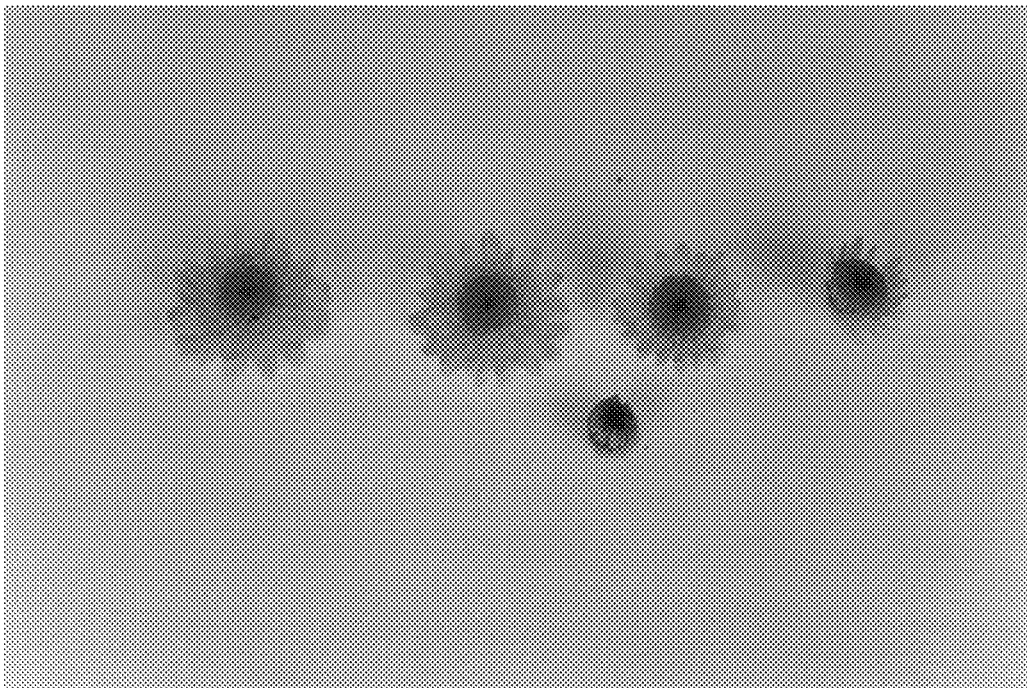
FIG. 2 shows the various stages of bloom of the new cultivar.
Figure 3:
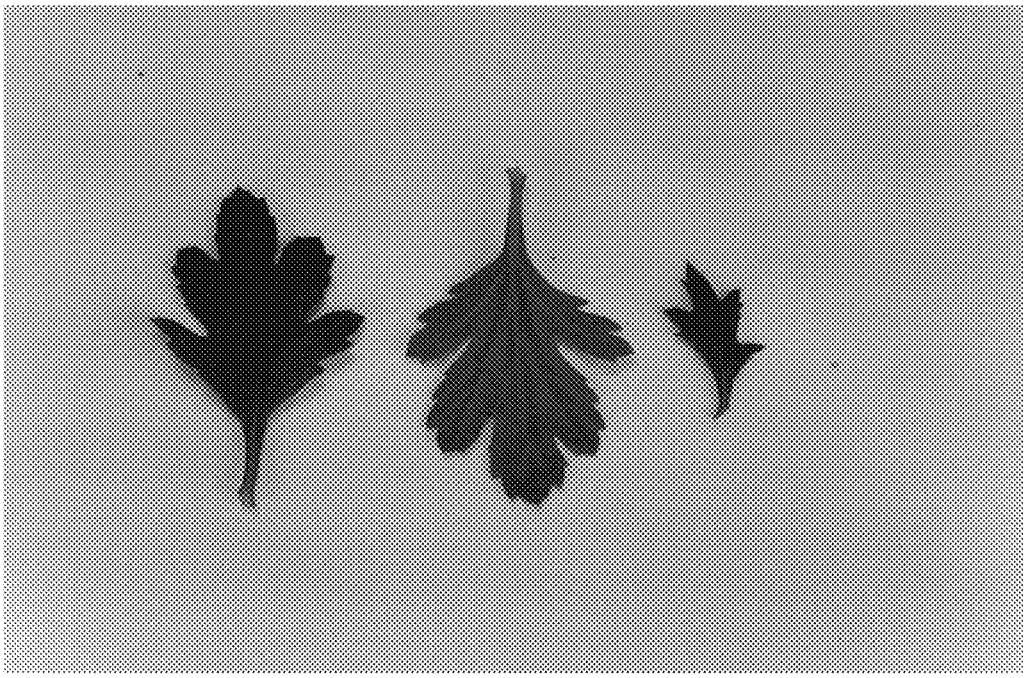
FIG. 3 shows the various stages of foliage and petiole of the new cultivar.

This new variety of chrysanthemum is of the botanical classi fication dendranthema grandiflora. The observations and measurements were gathered from 56 days plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 48 days after an average of eight long days. After this long day period to flowering growth retardants were applied 6 times in an average dose of 1.5 gram/liter water. The plants were observed (directly) during the flowering of this crop. No tests were done on disease or insect resistance or susceptibility. No tests were done on cold or drought tolerance. This new variety produces small sized blooms with yellow ray-florets and disc-florets grown to an anemone cushion of yellow color with brown tips, blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'CACHI DARK' can be planted without assimilation lightning (high pressure sodium lamps) between week 50 and week 40 of the next year uner greenhouse conditions in Holland. With assimilation light (minimum level 2500 lux) it can be planted year round under greenhouse conditions in Holland.

From the cultivars known to inventor the most similar existing cultivar in comparison to 'CACHI DARK' is CACHI. When CACHI and 'CACHI DARK' are being compared the following differences and similarities are noticed: The differences of CACHI and 'CACHI DARK' is-are the larger and darker brown spot on the center of the flower. For which characteristics 'CACHI DARK' has been selected out of CACHI. All other characteristics of CACHI and 'CACHI DARK' are similar.

The following is a description of the plant and characteristics that distinguish 'CACHI DARK' as a new and distinct variety. The color designations are taken from the plant itself. Accor dingly, any discrepancies between the color designations and the colors depicted in the photographs are due to photographic tolerances. The color chart used in this description is: The Royal Horticultural Society Colour Chart, edition 1995.

Botanical Description of CULTIVAR 'CACHI DARK'

Bud:
*Size*.—Small Cross-section 1.0 cm height 0.7 cm.
*Outside color*.—Yellow 13 B.
*Involucral bracts*.—2 rows, length 7 mm, width 3 mm.
*Involucral bracts among disc-florets*.—Not present.
*Involucral bracts color*.—Yellow-green 146 B.

Bloom:
*Type*.—Anemone.
*Height*.—Flat.
*Size*.—Small.
*Fully expanded*.—3.5–4.0 cm.
*Number of blooms per branch*.—Approx. 5 bloom.
*Performance on the plant*.—5 weeks.
*Seeds*.—Not produced.
*Fragrance*.—Typical chrysanthemum.

Color:
*Center of the flower* (*disc-florets*).—Immature greyed-red 181 A with a small portion of 183 A. Mature greyed-red 179 A.
*Color of upper surface of the ray-florets*.—Yellow 9 B.
*Color of the lower surface of the ray-florets*.—Yellow 5 C.
*Tonality from distance*.—A pot mum with small yellow flowers and a red-brown cushion.
*Discoloration to color*.—Ray-florets to Yellow 5 C, the cushion to Greyed-red 179 A.

Ray florets:
*Texture*.—Upper and under side fleshy smooth.
*Number*.—20–24.
*Cross-section*.—Concave.
*Longitudinal axis of majority*.—Incurving.
*Length of corolla tube*.—Very short.
*Ray-floret margin*.—Entire.
*Ray-floret length*.—1.5 cm.
*Ray-floret width*.—0.5.
*Ratio length/width*.—Medium.
*Shape of tip*.—Pointed.

Disc florets:
*Disc diameter*.—2.5 cm.
*Distribution of disc florets*.—Numerous clearly visible at all stages of flowering.
*Shape*.—Petaloid.
*Color*.—Yellow 7 A with greyed-red 181 A at the tip.
*Receptacle shape*.—Domed raised.

Reproductive organs:
*Stamen* (*present in disc florets only*).—Thin, 4 mm in length.
*Number of stamen*.—Grown together as one.
*Stamen color*.—Yellow-green 144 B.
*Pollen*.—None.
*Styles* (*present in both ray and disc florets*).—Thin.
*Style color*.—Yellow-green 144 B.
*Style length*.—5 mm.
*Stigmas*.—Yellow-green 144 B.
*Stigma width*.—5 mm.
*Ovaries*.—Enclosed in calyx.

Plant:
*Type*.—A pot mum meant for indoor use.
*Growth habit*.—Spreading.
*Growth rate*.—High.
*Height*.—20.0–22.0 cm.
*Width*.—24.0–26.0 cm.
*Stem color*.—Yellow-green 146 B.
*Stem strength*.—Medium.
*Stem brittleness*.—Present.
*Stem anthocyanin coloration*.—Present.
*Length of lateral branch*.—11.0 cm.
*Lateral branch, attachment*.—Medium (not weak, not strong).
*Branching* (*average number*).—Normal, with 4 breaks after pinching.
*Peduncle length*.—2.5 cm.
*Peduncle color*.—Yellow-green 146 B.
*Flowering response* (*photo-periodic controlled crop, not natural season*).—48 days.

Foliage:
*Color*.—Upper side yellow-green 147 A. Under side yellow-green 147 B.
*Size*.—Small; length 5.0 cm, width 4.0 cm.
*Quantity* (*number per lateral branch*).—8–10.
*Shape*.—Oval.
*Texture upper side*.—Glabrous.
*Texture under side*.—Pubescent.
*Venation arrangement*.—Palmate.
*Shape of the margin*.—Serrated.
*Shape of base of sinus between lateral lobes*.—Round.
*Margin of sinus between lateral lobes*.—Diverging.
*Shape of base*.—Attenuate.
*Apex*.—Cuspidate.

Differences with the comparison Varieties

| | 'CACHI' | 'CACHI DARK' |
|---|---|---|
| Color of the center of the flower | Greyed-orange 166 C | Greyed-red 181 A with a small portion of 183 A |

I claim:

1. A new and distinct variety of chrysanthemum plant as described and illustrated.

* * * * *